United States Patent [19]

Kar et al.

[11] Patent Number: 5,230,964
[45] Date of Patent: * Jul. 27, 1993

[54] MAGNETIC RECORDING MEDIA A COMPRISING MAGNETIC PARTICLES BINDER AND (FLUORINATED PHENOXY)(3-PERFLUOROALKYL-PHENOXY)-CYCLIC PHOSPHAZENE LUBRICANT

[75] Inventors: Kishore K. Kar, Midland; Chester E. Pawloski, Bay City; Ted A. Morgan, Midland, all of Mich.

[73] Assignee: The Dow Chemical Company, Midland, Mich.

[ * ] Notice: The portion of the term of this patent subsequent to May 14, 2008 has been disclaimed.

[21] Appl. No.: 630,678

[22] Filed: Dec. 20, 1990

Related U.S. Application Data

[63] Continuation-in-part of Ser. No. 417,363, Oct. 10, 1989, Pat. No. 5,015,408.

[51] Int. Cl.$^5$ .............................................. G11B 05/00
[52] U.S. Cl. ...................................... 428/694; 428/900
[58] Field of Search ........................ 428/694, 695, 900

[56] References Cited

U.S. PATENT DOCUMENTS

| | | |
|---|---|---|
| 2,109,491 | 3/1938 | Lipkin . |
| 2,192,921 | 3/1940 | Lipkin . |
| 2,214,769 | 9/1940 | Lipkin . |
| 2,876,247 | 3/1959 | Ritz et al. . |
| 3,136,727 | 6/1964 | Nichols ............................ 252/49.9 |
| 3,201,445 | 8/1965 | Drydale et al. . |
| 3,234,304 | 2/1966 | Nichols . |
| 3,251,538 | 5/1966 | Barnitz . |
| 3,280,222 | 10/1966 | Kober et al. . |
| 3,291,865 | 12/1966 | Kober et al. . |
| 3,313,731 | 4/1967 | Dolle et al. ...................... 252/49.7 |
| 3,316,330 | 4/1967 | Nichols . |
| 3,334,046 | 8/1967 | Dexter et al. .................... 252/47.5 |
| 3,395,147 | 7/1968 | Cornell . |
| 3,397,204 | 8/1968 | Gaertner . |
| 3,459,838 | 8/1969 | Klender . |
| 3,682,908 | 8/1972 | Ismall . |
| 3,687,952 | 8/1972 | Ismall . |
| 4,029,634 | 6/1977 | Meredith . |
| 4,600,791 | 7/1986 | Carr et al. . |
| 4,601,843 | 7/1986 | Carr et al. ...................... 252/78.5 |
| 4,613,548 | 9/1986 | Lum .............................. 428/411.1 |
| 4,645,615 | 2/1987 | Drake ............................ 252/78.5 |
| 4,698,439 | 10/1987 | Kolich et al. .................... 558/80 |
| 4,724,264 | 2/1988 | Nakacho et al. ................ 558/80 |
| 4,727,175 | 2/1988 | Bezoari ........................... 558/80 |
| 4,727,176 | 2/1988 | Bezoari ........................... 558/80 |
| 4,871,625 | 10/1989 | Dekura et al. .................. 428/695 |
| 5,015,405 | 5/1991 | Kar et al. ....................... 252/49.9 |

FOREIGN PATENT DOCUMENTS

| | | |
|---|---|---|
| 1053336 | 4/1987 | European Pat. Off. . |
| 111704 | 7/1981 | Japan . |
| 103543 | 5/1985 | Japan . |
| 145272 | 7/1985 | Japan . |

OTHER PUBLICATIONS

Chemical Abstracts, 1979, vol. 91, p. 785.
Chemical Abstracts, 1983, vol. 98, p. 34.
Chemical Abstracts, 1984, vol. 101, p. 714.
Chemical Abstracts, 1988, vol. 108, p. 247.
Chemical Abstracts, 1973, vol. 78, p. 399.
Derwent Publications Ltd., ADW DER DDR, Nov. 1980.
Letin, A. S. et al., "Organooxy cyclotriphosphazenes as an additive for lubricating oils", Khim. Technol. Topl. Masel 1980, (9) 24-5.

*Primary Examiner*—Paul J. Thibodeau
*Assistant Examiner*—Stevan A. Resan
*Attorney, Agent, or Firm*—Robert M. O'Keefe

[57] ABSTRACT

A magnetic recording media containing a lubricant which is a cyclic phosphazene completely substituted with fluorinated phenoxy substituents and m-perfluoroalkylphenoxy substituents, in ratios ranging from 1:1 to 1:5 is disclosed. The recording media and lubricant are particularly useful for advanced, high density magnetic recording media.

19 Claims, 1 Drawing Sheet

FIG 1

MAGNETIC RECORDING MEDIA A COMPRISING MAGNETIC PARTICLES BINDER AND (FLUORINATED PHENOXY)(3-PERFLUOROALKYLPHENOXY)- CYCLIC PHOSPHAZENE LUBRICANT

CROSS REFERENCE TO RELATED APPLICATION

This application is a continuation-in-part of Ser. No. 07/417,363 now U.S. Pat. No. 5,015,408 filed Oct. 10, 1989, which is hereby incorporated by reference.

TECHNICAL FIELD

This invention relates generally to magnetic recording media and performance lubricants therefore, but more particularly relates to recording media containing fluorinated phenoxy substituted cyclic phosphazenes.

BACKGROUND OF THE INVENTION

Magnetic recording media such as high density rigid disks, ultra high density floppy disks, digital audio tapes and video tapes can be read by a magnetic recording head as the recording media moves past the recording head. The recording head is in very close proximity to the recording media and frequently contacts the recording media. Such contact causes wear of the thin layer of magnetic material on the recording media and shortens the useful life of the recording media. Older technology media types such as standard audio, VHS video and standard floppy disks experience wear problems due to unsuitable lubricants. These problems included increased friction, scratching and adhesion. Such problems are addressed by the new, more efficient internal and boundary lubricant systems of the present invention. The lubricant of the present invention is designed to be used with the more advanced forms of magnetic recording media mentioned above.

Another important characteristic of a phosphazene lubricant for magnetic media is solvent compatibility of the lubricant. The lubricant must be dissolvable in solvents such as tetrahydrofuran and acetone. The lubricant must also be stable in the presence of water and base.

Lubricants for magnetic media are known in the art, but such lubricants are limited to those for more mature counter-parts of the magnetic media such as standard audio, VHS video and standard floppy disks. Furthermore, these lubricants do not demonstrate solvent compatibility with a wide range of organic solvents and are not stable in water and base. Examples of such lubricants are described in U.S. Pat. No. 4,613,548 to Lum, issued on Sep. 23, 1986, which discloses a magnetic recording media containing a normally liquid phosphazene lubricant, e.g. low molecular weight linear or cyclic polyfluoroalkoxy phosphazene mixtures. Such fluoroalkoxy substituted phosphazenes as recited in the Lum reference do not exhibit the stability of the present invention in bases and water.

U.S. Pat. No. 4,029,634 to Meredith discloses a flame retardant composition for a polymer including a halogen substituted hexakis-(substituted phenoxy) cyclotriphosphazene in the polymer. The halogenated phenoxy substituent utilizes either bromine or chlorine.

U.S. Pat. No. 4,601,843 to Carr et al. discloses a cyclic phosphazene based functional fluid which exhibits fire resistance, fluidity and compatibility with engine seal compositions. The phosphazene is substituted with at least one alkoxy moiety and three different moieties which may include a fluorinated phenoxy moiety or a fluoroalkylphenoxy moiety among various other compounds.

U.S. Pat. No. 3,291,865 to Kuber et al. discloses cyclic polymeric phosphonitrilate compositions substituted with a first substituent which is a polyfluoroalkoxy compound and a second substituent which may include a halogenated lower alkyl-substituted phenoxy or a halogen substituted phenoxy.

U.S. Pat. No. 3,316,330 to Nichols, discloses a polymeric phosphonitrile substituted with a meta-trifluoromethoxyphenoxy substituent and a phenoxy substituent. The composition is useful as a working fluid, a high temperature lubricant and a plasticizer.

It is a primary object of the present invention to provide a solvent compatible, magnetic recording media lubricant, including a cyclic phosphazene completely substituted with fluorinated phenoxy moieties. An additional object of the invention is to provide a lubricant which is stable in bases and water and at high temperatures.

Yet another object of the present invention is to provide high density, state of the art recording media, such as high density rigid disks, ultra high density floppy disks, digital audio tape, 8 mm video tape and super VHS tape including a lubricant which may be used as an internal or boundary lubricant system to minimize wear and improve overall performance.

SUMMARY OF THE INVENTION

In accordance with the preferred embodiment of the invention, these and other objects and advantages are addressed as follows.

The magnetic recording media of the present invention utilizes a phenoxy substituted cyclic phosphazene lubricant as an internal and boundary lubricant for state of the art, high density recording media.

The magnetic recording media containing the phenoxy substituted phosphazene comprises a substrate; a magnetic recording media thereon which includes magnetic particles for recording information; a binder for suspending the magnetic particle and a cyclic phosphazene having the formula wherein n is 3 through 7 and R is individually in each occurrence one or more (1) fluorinated phenoxy substituents selected from the group consisting of monofluorinated phenoxy, difluorinated phenoxy, trifluorinated phenoxy, tetrafluorinated phenoxy and pentafluorinated phenoxy substituents; and (2) one or more m-perfluoroalkylphenoxy substituents. The substituents are present in a ratio of fluorinated phenoxy to m-perfluoroalkyl phenoxy ranging from about 1:1 to about 1:5.

The lubricant is utilized in an internal boundary system by preparing a lubricant containing lamina for application to a recording substrate. The lamina is prepared by forming a dispersion of solvent, a pigment containing magnetic particles and a urethane-vinyl binder system. The lamina is then applied to a polyester base film.

Alternatively, the cyclophosphazene lubricant may be used as a surface lubricant. The lubricant is applied to the surface of the recording lamina and allowed to impregnate the recording media.

Advantages of the recording media containing the fluorophenoxy substituted cyclophosphazene lubricant of the present invention are the improved physical and magnetic durabilities due to the more effective lubrication. In addition, another advantage arises with processability in manufacturing because the phenoxy substituted moieties render the cyclophosphazene lubricants solvent compatible in organic solvents such as toluene and acetone. This makes the product more practical and economical to produce. Furthermore, the fluorophenoxy substituent on the cyclophosphazene renders the lubricant stable in bases and water unlike fluoroalkoxy substituted cyclophosphazenes of the prior practices. These advantages and objects will be further discussed in the detailed description which follows.

BRIEF DESCRIPTION OF THE DRAWINGS

The nature and extent of the present invention will be clear from the following detailed description of the particular embodiments thereof, taken in conjunction with the appendant drawing, in which.

DETAILED DESCRIPTION OF THE INVENTION

A preferred embodiment of the present invention is a magnetic recording media comprising a substrate having a magnetic recording lamina thereon, the lamina comprising magnetic particles and a binder. The lamina includes a lubricating amount of a cyclic phosphazene which may be used as either an internal or boundary lubricant. Effective phosphazenes for this purpose are substituted with fluorinated phenoxy moieties and 3-perfluoralkyl-phenoxy moieties on the phosphazene ring.

The cyclic phosphazenes of the present invention are preferably trimeric although higher oligomers such as tetrameres may be used. When the trimeric oligomers are used, they may also contain minor amounts of higher oligomers.

The cyclic phosphazenes preferably correspond to the formula:

wherein n is 3 through 7, R is individually in each occurrence fluorinated phenoxy and 3-perfluoroalkylphenoxy such that the ratio of fluorinated phenoxy to 3-perfluoroalkylphenoxy ranges from about 1:5 to about 1:1.

The fluorinated phenoxy moieties contain from one to five fluorine atoms. It is preferred that the fluorinated phenoxy moiety contain one fluorine atom and that the fluorine atom is ortho, meta or para to the oxygen atoms of the phenoxy moiety. The perfluoroalkyl group of the meta-perfluoroalkylphenoxy is preferably a lower perfluoroalkyl group having from one to about five carbon atoms and is most preferably a trifluoromethyl group.

The ratio of fluorinated phenoxy to perfluoroalkyl-phenoxy substituents ranges from about 1:5 to about 1:1. It is preferred that the ratio ranges from about 1:2 to about 1:1. It is more preferred that the ratio is about 1:2.

While the compounds of the present invention are described as single molecules having specified substituents present in a stated ratio, it will be realized by one skilled in the art that the compounds will exist as statistical mixtures of molecules. Some of these molecules will have the specified ratio of substituents while others will have higher or lower ratios. However, the phosphazenes will, within these statistical mixtures, have substituents present at the specified ratios.

The following are non-limiting examples of the cyclic phosphazenes of this invention wherein the m-perfluoroalkylphenoxy substituent includes the 3-trifluoromethylphenoxy moiety. These examples include 2,2,4,4,6,6-mono(fluorophenoxy)penta(3-trifluoromethyl-phenoxy)-1,3,5-triaza -2,4,6 triphosphorine; 2,2,4,4,6,6-di(4-fluorophenoxy)tetra(3-trifluoromethylphenoxy)-1, 3,5-triaza-2,4,6-triphosphorine; 2,2,4,4,6,6-di(3-fluorophenoxy)tetra(3-trifluoromethylphenoxy)-1,3,5-triaza-2,4,6-triphosphorine; 2,2,4,4,6,6-(3-fluorophenoxy) (4-fluorophenoxy) tetra(3-trifluoromethylphenoxy)-1,3,5-triaza-2,4,6-triphosphorine; 2,2,4,4,6,6-di(2-fluorophenoxy)tetra(3-trifluoromethylphenoxy)-1,3,5-triaza; 2,4,6-triphosphorine; 2,2,4,4,6,6-tri(2-fluorophenoxy)tri(3-trifluoromethylphenoxy)-1,3,5-triaza-2,4,6-triphosphorine; 2,2,4,4,6,6-tri(3-fluorophenoxy)tri(3-trifluoromethylphenoxy)-1,3,5-triaza-2,4,6-triphosphorine; 2,2,4,4,6,6-tri(4-fluorophenoxy)-tri(3-trifluoromethylphenoxy)-1,3,5-triaza-2,4,6-triphosphorine; 2,2,4,4,6,6,8,8-tri(4-fluorophenoxy)penta(3-trifluoromethylphenoxy)-1,3,5, 7-triaza-2,4,6,8-tetraphosphorine; 2,2,4,4,6,6,8,8-tri(3-fluorophenoxy)penta(3-trifluoromethylphenoxy)-1, 3,5,7-tetraza-2,4,6,8-tetraphosphorine; 2,2,4,4,6,6, 8,8-tetra(4- fluorophenoxy)tetra(3-trifluoromethylphenoxy)-1,3,5,7-tetraza-2,4,6,8-tetraphosphorine; 2,2,4,4,6,6,8,8-tetra(3-fluorophenoxy)tetra(3-trifluoromethylphenoxy)-1,3,5, 7-tetraza-2,4,6,8-tetraphosphorine; 2,2,4,4,6,6,8,8-2.57(3-fluorophenoxy)-5.43(3-trifluoromethylphenoxy)-1,3,5,7-tetraza-2,4,6,8-tetraphosphorine; 2,2,4,4,6,6,8,8-2.57(4-fluorophenoxy)-5.43(3-trifluoromethylphenoxy)-1,3,5,7-tetraza-2,4,6,8-tetraphoshorine and mixtures thereof.

In a preferred embodiment, the phosphazene is 2,2,4,4,6,6-di(3- fluorophenoxy)tetra(m-trifluoromethylphenoxy)-1,3,5-triaza-2,4,6-triphosphorine, 2,2,4,4,6,6-di(4-fluorophenoxy)tetra(m-trifluoromethylphenoxy)-1,3,5-triaza-2,4,6-triphosphorine or mixtures thereof.

The lubricants may be prepared by methods known in the art. It is preferred that they are prepared in a one-pot, two-stage reaction. In the first stage, a fluorinated phenol and a perfluoroalkylphenol are placed into a flask with a solvent. An alkali metal hydroxide is added and the mixture is allowed to reflux and the waters of reaction are removed. The mixture is then allowed to cool and a halogenated cyclic phosphazene is added and the mixture is refluxed. The product is then recovered using conventional techniques. The fluorinated phenol, perfluoroalkylphenol and halogenated phosphazene starting materials are commercially available or may be prepared using conventional techniques.

In the preparation of the compounds of this invention, the fluorinated phenol, the perfluoroalkylphenol and the halogenated phosphazene reactants are used in amounts sufficient to insure that the fluorinated phenol and perfluoroalkylphenol are present in a ratio of from about 1:1 to about 1:2 and the fluorinated phenol and perfluoroalkylphenol completely replace the halogens on the phosphazene ring. For example, when the phosphazene is a trimer such as 2,2,4,4,6,6-hexachloro-1,3,5-triaza-2,4,6-triphosphorine, it is preferred to use at least about two moles of fluorinated phenol and at least about four moles of perfluoroalkylphenol per mole of 2,2,4,4,6, 6-hexachloro-1,3,5-triaza-2,4,6-triphosphorine. When the phosphazene is a tetramer, it is preferred to use at least about 2.6 moles of fluorinated phenol and at least about 5.4 moles of perfluoroalkylphenol per mole of 2,2,4,4,6,6,8,8-octachloro-1,3,5,7-tetraza-2,4,6,8-tetraphosphorine. It is preferred to use a slight stoichiometric excess each of fluorinated phenol and perfluoroalkylphenol to insure complete reaction.

Turning now to the application of the lubricant to the present invention, magnetic recording media generally include a substrate which may be a nonmagnetic metal or a plastic such as polyester. Magnetic particles such as cobalt gamma $Fe_2O_3$, barium ferrite or iron metal and the like, together with a binder are applied to the substrate. The amount of magnetic particles can vary from about 17.0 to about 21.0 weight percent based on total formulation weight. The preferred range is from about 17.0 to about 19.0 weight percent. The binder is usually a thermosetting resin such as urethane, vinyl or a combination thereof, present in an amount between about 2.5 and about 6.0 weight percent, based on total formulation weight. The preferred range is between about 3.0 and about 6.0 weight percent.

When used as an internal lubricant, the fluorphenoxycyclophosphazene lubricant is included in the composition of the mixture applied to the substrate to form the recording lamina. This mixture includes binder, magnetic particles and a volatile solvent together with the fluorophenoxycyclophosphazene lubricant. Suitable solvents for the lubricant include aromatic hydrocarbons (e.g. toluene), ethers (e.g. diethylether, dimethyloxyethane, dioxane, tetrahydrofuran, diethoxyethane), halogenated hydrocarbons, alcohols, ketones (e.g. acetone), esters, alicyclic hydrocarbons, dimethyl formamide and dimethyl sulfoxide.

The lubricant containing magnetic media of the present invention were prepared in the following way. A dispersion comprising a urethane-vinyl binder and magnetic particles was prepared in tetrahydrofuran solvent. Three types of magnetic particles were used: iron metal, barium ferrite and cobalt gamma $Fe_2O_3$, utilizing magnetic particles to binder ratios of between 3:1 and 8:1. Magnetic particles were present in an amount from about 2.5 to about 6.0 weight percent based on total formulation weight. Lubricant was added to the dispersion in an amount between 0 and 5 weight percent of total formulation weight. A surfactant was added to the composition in an amount between about 0.50 and about 1.0 weight percent of total formulation weight. The magnetic particles were orientated by application of a magnetic field. The solvent was evaporated and the polymer binder was cured by a thermal process.

Alternatively, the lubricant described herein can be used in thin film, or non-porous hard and flexible magnetic media and is not limited to porous media containing a binder.

In another embodiment, cyclic phosphazene lubricants were applied to the surface of the recording lamina and allowed to impregnate the lamina.

Samples containing the internal boundary fluorinated phenoxy lubricant of the present invention were compared with identical samples prepared with Krytox 143AD, a hexafluoropropylene epoxide polymer available from DuPont DeNemeurs Co., Wilmington, Del., and samples prepared with isocetyl stearate (hereinafter ICS). The surface treated media containing the lubricant of the present invention were compared with media surfaces treated with Krytox 143 AD. Both boundary lubricant media and surface treated media were evaluated for physical and magnetic properties. Physical properties included sliding friction, scratch resistance, adhesion and Steinberg tension-time to fail test. The results of these tests are set forth in examples 4-7.

Magnetic properties evaluated were coercivity, squareness, remanence and saturation. Magnetic properties are reflected in the response of the medium to an applied magnetic field. This response takes the form of the magnetic hysteresis loop found in FIG. 1. The hysteresis loop plots magnetization of a material to which a magnetic field is applied. At first the material magnetization increases from 0 (a) to a maximum, or saturation (c). If the strength of the field is then decreased, the magnetization persists. A reversal of the field drives the material to saturation with magnetism oriented in the opposite direction.

Figure 1:
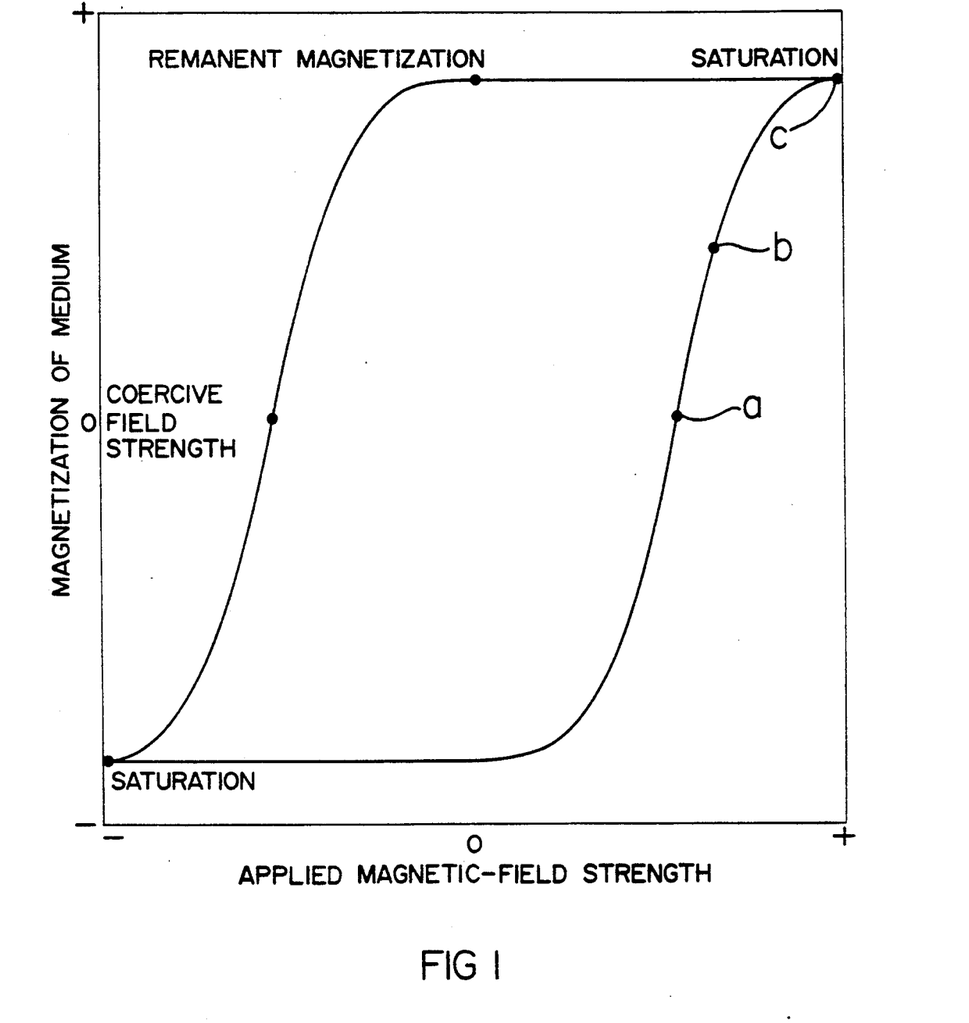
FIG. 1 shows a hysteresis loop which defines the magnetic properties of the recording media.

There are four parameters that characterize such a loop: (1) the first is the value of magnetization at very high fields, the saturation magnetization, $m_f$. This should correspond to the magnetic moment per unit volume;

(2) the second parameter is the remanent magnetization which depends upon the domain structure in a zero field;

(3) the third parameter is the coercivity or the value of the applied field required to drive the magnetization to zero. Coercivity varies and is a strong function of chemical and structural defects. For permanent magnets, high coercivities are desirable. Typical coercivities for recording media are in the vicinity of 500-800 Oersted (Oe); and (4) the fourth parameter is squareness which equals the value of the remanent magnetization divided by the value for the saturation magnetization.

The magnetic recording media containing the phosphazene lubricant of the present invention demonstrate improved durability and dispersion performance. This is shown in the laboratory sample test results set forth in Example 6. The barium ferrite magnetic media containing fluorinated cyclophosphazene demonstrated improved performance in the areas of magnetics, when compared to barium ferrite containing ICS or no lubricant.

The cyclophosphazene lubricants also showed improved durability when used as a surface coating for the magnetic media. As shown in Example 7, magnetic particles treated with fluorinated cyclophosphazene lubricant demonstrated reduced friction and increased resistance to scratching in comparison to pigments treated with KRYTOX 143AD.

The results of our experiments show that magnetic media containing cyclophosphazene lubricants are far superior to other commercially available products in that these lubricants provide optimal physical and magnetic performance and are economical to produce. Furthermore, from our experiments it appears that the fluorophenoxy substituents exhibit enhanced lubricant stability in bases and water.

The following examples are provided for illustrative purposes only and should not be construed as limiting the invention in any way. Unless stated otherwise, all parts and percentages are by weight.

EXAMPLES

EXAMPLE 1

Preparation of Cyclophosphazene Lubricants: Preparation of 2,2,4,4,6,6-di(4-fluoro-phenoxy)-tetra(3-trifluoromethylphenoxy)-1,3,5-triaza-2,4,6-triphosphorine A 5.6-g (0.05 mole) portion of 4-fluorophenol and 16.2 g (0.1 mole) 3-trifluoromethylphenol were placed into a flask with 100 ml of toluene and 150 ml of xylene. The flask was equipped with a stirrer and a Dean-Stark trap and 9.6 g (0.15 mole) of potassium hydroxide were added. The mixture was stirred at reflux until waters of reaction cease to evolve. The mixture was then allowed to cool to 100° C. and 8.7 g (0.025 moles) of 2,2,4,4,6,6-hexachloro-1,3,5-triaza-2,4,6-triphosphazene were added in portions as a solid at such a rate to prevent the solvent from distilling from the flask. After this, the mixture was refluxed for 16 hours. After cooling, the product was stirred with 1 liter of dilute NaOH water solution, separated and then stirred with 1 liter of water. The product phase was separated, dried over sodium sulfate, filtered and low boilers were distilled and saved. The product, 2,2,4,4,6,6-di(4-fluorophenoxy)-tetra(3-trifluoromethylphenoxy)-1,3,5-triaza-2,4,6-triphosphorine, was further distilled at 250° C. and 0.1 mm Hg to produce an oil with a pour point at $-10°$ C. and a thermal stability of 429° C. by DSC.

EXAMPLE 2

Preparation of 2,2,4,4,6,6-di(3-fluorophenoxy)tetra(3-trifluoromethyl phenoxy)-1,3,5-triaza-2,4,6-triphosphorine:

A 56 g (0.5 mole) portion of 3-fluorophenol and 162 g (1.0 moles) of 3-trifluoromethyl phenol were placed in a flash with 500 ml xylene, 200 ml toluene and 50 ml diglyme. The flask was equipped with a stirrer and a Dean-Stark trap. To this mixture was added 84 g (1.5 moles) of potassium hydroxide. The mixture was stirred at reflux until waters of reaction ceased to evolve. The mixture was then allowed to cool to 100° C., and 87 g. (0.25 mole) of hexachloro 1,3,5-triaza-2,4,6-triphosphorine in solid form, was added, in portions at a rate to prevent the solvent from distilling from the flask. After this the mixture was reflexed for 16 hours. After cooling, the product was stirred with 1 liter of delute NaOH water solutions separted and then stirred with 1 liter of water. The product phase was separated, dried over sodium sulfate, filtered and low boilers were distilled and saved. The product was an oil having a pour point at $-15°$ C. and a boiling point of 250°-260° C. at 5 mm Hg.

EXAMPLE 3

Preparation of mixture of 4/1 mole ratio of 2,2,4,4,6,6-(2/1 mole ratio of 3-fluorophenoxy/4-fluorophenoxy)tetra(3-trifluoromethylphenoxy)-1,3,5-triaza-2,4,6-triphosphorine and 2,2,4,4,6,6,8,8-2.57(2/1 mole ratio of 3-fluorophenoxy/4-fluorophenoxy)-5.43(3-trifluoromethyl-phenoxy)-1,3,5, 7-tetraza-2,4,6,8-tetraphosphorine A 26.3-g (0.23 mole) portion of a 2/1 mole ratio of 3-fluorophenol/4-fluorophenol and 76 g (0.47 mole) 3-trifluoromethylphenol were placed into a flask with 50 ml of diglyme and 500 ml of xylene. The flask was equipped with a stirrer and a Dean-Stark trap and 46 g (0.7 mole) of potassium hydroxide was added. The mixture was stirred at reflux until waters of reaction ceased to evolve. The mixture was then allowed to cool to 100° C. and 27.8 g (0.02 moles) of 2,2,4,4,6,6-hexachloro-1,3,5-triaza-2,4,6-triphosphazene and 27.8 g (0.08) mole of 2,2,4,4,6,6,8,8-octachloro-1,3,5,7-tetraza-2,4,6,8-tetraphosphazene were added in portions as a solid at such a rate to prevent the solvent from distilling from the flask. After this, the mixture was refluxed for 16 hours. After cooling, the product was stirred with 1 liter of dilute NaOH water solution, separated and then stirred with 1 liter of water. The product phase was separated, dried over sodium sulfate, filtered and low boilers were distilled and saved. The product was distilled to produce an oil with a pour point at $-18°$ C. and boiling point of 285° C. at 0.5 mm Hg.

EXAMPLE 4

Dispersion Formulations To Determine Performance at Various Lubricant Levels

Experimental samples of magnetic media were prepared in jar mills to simulate milling conditions on various test formulations. Dispersions of the urethane-vinyl binder and the magnetic particles (cobalt gamma $Fe_2O_3$, iron metal, and barium ferrite) were prepared in tetrahydrofuran. Various samples were prepared using: (1) no lubricant; (2) isocetyl stearate designated as Lubricant II and (3) the fluorophenoxycyclophosphazene lubricant of the present invention, designated as Lubricant I. Media samples A, B and C utilized Lubricant II, D, E and F utilized Lubricant I, and G contained no lubricant. The dispersions were milled for a period of 4 days in a laboratory jar mill and coated onto polyester film.

The coatings were cured and tested while on the film, for:

Coefficient of friction
Steinberg video still frame durability (8 min./sec 50 grams tension; time to fail in minutes)
Adhesion
Scratch resistance (particle loading in grams)
Magnetic properties

TABLE A

The first set of experiments performed utilized various lubricant concentrations. The magnetic particles to binder weight ratio was 4:1 for all samples. All samples are in weight percent. The formulations for the various dispersions were prepared as follows:

| FORMULATIONS | PRIOR ART | | | PRESENT INVENTION | | | NO LUBE |
|---|---|---|---|---|---|---|---|
| | A | B | C | D | E | F | G |
| Magnetic Particles | 18.26 | 18.23 | 18.19 | 18.26 | 18.23 | 18.19 | 18.36 |
| SURFACTANT[b] (Re 61-GAF Corp.) | 0.55 | 0.55 | 0.55 | 0.55 | 0.55 | 0.55 | 0.55 |
| LUBRICANT I (cyclophosphazene lube) | 0 | 0 | 0 | 0.55 | 0.73 | 0.91 | 0 |
| URETHANE[c] BINDER (ESTANE 5701) | 3.04 | 3.04 | 3.03 | 3.04 | 3.04 | 3.03 | 3.06 |
| VAGH (Vinyl Acetate[d]/vinyl chloride copolymer | 1.52 | 1.52 | 1.52 | 1.52 | 1.52 | 1.52 | 1.53 |
| THF[e] | 76.08 | 75.94 | 75.80 | 76.08 | 75.94 | 75.80 | 76.50 |

TABLE A-continued

The first set of experiments performed utilized various lubricant concentrations. The magnetic particles to binder weight ratio was 4:1 for all samples. All samples are in weight percent. The formulations for the various dispersions were prepared as follows:

| FOR-MULATIONS | PRIOR ART | | | PRESENT INVENTION | | | NO LUBE |
|---|---|---|---|---|---|---|---|
| | A | B | C | D | E | F | G |
| LUBRICANT II (Isocetyl Stearate) | 0.55 | 0.73 | 0.91 | 0 | 0 | 0 | 0 |

[a] Magnetic Particles used: iron metal; barium ferrite; cobalt gamma $Fe_2O_3$.
[b] Re 610 is a registered trademark of GAF Corp. of NY, NY.
[c] Estane is a registered trademark of B. F. Goodrich Chemical Group, Cleveland, OH.
[d] VAGH is the vinyl acetate/vinylchloride copolymer component of the urethane-vinyl binder a registered trademark of Union Carbide Corp., Danforth, Conn.
[e] Tetrahydrofuran.

TABLE B

Physical Test Results
The following test results are a comparison of physical performance of the media containing internal boundary Lubricants I and II and no lubricant.

| Magnetic Particles | SLIDING FRICTION | SCRATCH RESISTANCE | ADHESION | STEINBERG 8 min/Sec 50 gm. TENSION-TIME TO FAIL IN MIN. |
|---|---|---|---|---|
| IRON METAL | | PRIOR ART | | |
| A | 0.28 | 400 | PASS | 16 |
| B | 0.28 | 500 | PASS | 12 |
| C | 0.33 | 500 | PASS | 10 |
| | | PRESENT INVENTION | | |
| D | 0.28 | 400 | PASS | 28 |
| E | 0.31 | 500 | PASS | 21 |
| F | 0.34 | 450 | PASS | 20 |
| | | NO LUBRICANT | | |
| G | 0.34 | 300 | FAIL | 4 |
| BARIUM FERRITE | | PRIOR ART | | |
| A | 0.33 | 400 | PASS | 18 |
| B | 0.34 | 300 | PASS | 16 |
| C | 0.36 | 300 | PASS | 16 |
| | | PRESENT INVENTION | | |
| D | 0.33 | 500 | PASS | 26 |
| E | 0.34 | 500 | PASS | 25 |
| F | 0.36 | 500 | PASS | 21 |
| | | NO LUBRICANT | | |
| G | 0.34 | 100 | FAIL | 6 |
| COBALT GAMMA $Fe_2O_3$ | | PRIOR ART | | |
| A | 0.33 | 500 | PASS | 20 |
| B | 0.34 | 500 | PASS | 21 |
| C | 0.36 | 450 | PASS | 21 |
| | | PRESENT INVENTION | | |
| D | 0.33 | 450 | PASS | 27 |
| E | 0.34 | 550 | PASS | 29 |
| F | 0.36 | 500 | PASS | 26 |
| | | NO LUBRICANT | | |
| G | 0.34 | 100 | FAIL | 4 |

(*KEY A, B, C, = Lubricant II (isocetyl stearate) D, E, F = Lubricant I (cyclophosphazene lube) G = No Lubricant)

TABLE C

The following test results demonstrate the magnetic properties of recording media containing internal boundary Lubricant I and II and no lubricant. Magentic properties are defined on a hysteresis test loop and as set forth hereinabove to reference with FIG. 1.

Magnetic Test Results

| MAGNETIC PARTICLES | COERCIVITY | SQUARENESS | REMANENCE | SATURATION |
|---|---|---|---|---|
| IRON METAL | | PRIOR ART | | |
| A | 650 | 0.79 | 2670 | 3069 |
| B | 650 | 0.78 | 2596 | 2953 |
| C | 650 | 0.71 | 2303 | 3641 |
| | | PRESENT INVENTION | | |
| D | 660 | 0.74 | 2341 | 3164 |
| E | 650 | 0.73 | 2094 | 2869 |
| F | 625 | 0.73 | 1508 | 2067 |
| | | NO LUBRICANT | | |
| G | 730 | 0.75 | 2600 | 3206 |
| BARIUM FERRITE | | PRIOR ART | | |
| A | 750 | 0.91 | 1570 | 2095 |

TABLE C-continued

The following test results demonstrate the magnetic properties of recording media containing internal boundary Lubricant I and II and no lubricant. Magentic properties are defined on a hysteresis test loop and as set forth hereinabove to reference with FIG. 1.

Magnetic Test Results

| MAGNETIC PARTICLES | COERCIVITY | SQUARENESS | REMANENCE | SATURATION |
|---|---|---|---|---|
| B | 790 | 0.91 | 1070 | 1582 |
| C | 725 | 0.91 | 980 | 1424 |
| | | PRESENT INVENTION | | |
| D | 800 | 0.94 | 1340 | 2144 |
| E | 790 | 0.93 | 1106 | 2060 |
| F | 750 | 0.95 | 1200 | 1980 |
| | | NO LUBRICANT | | |
| G | 905 | 0.87 | 1390 | 2144 |
| COBALT GAMMA $Fe_2O_3$ | | PRIOR ART | | |
| A | 575 | 0.85 | 1180 | 2215 |
| B | 550 | 0.86 | 1291 | 2532 |
| C | 540 | 0.86 | 1347 | 3509 |
| | | PRESENT INVENTION | | |
| D | 525 | 0.90 | 1308 | 2560 |
| E | 500 | 0.90 | 1308 | 2560 |
| F | 500 | 0.91 | 1049 | 2250 |
| | | NO LUBRICANT | | |
| G | 625 | 0.80 | 1052 | 1793 |

SUMMARY OF TEST RESULTS

The physical test results show that the desirable smaller values for friction are exhibited by iron metal magnetic particles treated with respectively, 0.55 and 0.73 weight percent of Lubricant II (ICS), and with 0.55 weight percent of Lubricant I of the present invention. Barium ferrite magnetic particles treated with identical amounts of Lubricant II and Lubricant I give identical results, as do the cobalt gamma $Fe_2O_3$ samples.

The larger values for scratch resistance are desirable as they indicate greater scratch resistance. Iron metal magnetic particles treated with 0.73 weight percent and 0.91 weight percent of Lubricant II and Lubricant I, respectively, give identical results and provide the best scratch resistance. Lubricant I achieves slightly better results at 0.91 weight percent. Barium ferrite magnetic particles treated with Lubricant II of the present invention demonstrated scratch resistance superior to any of the magnetic particles samples treated with Lubricant I. Cobalt gamma $Fe_2O_3$ magnetic particles treated with 0.73 weight percent of Lubricant II exhibited the best scratch resistance. All samples passed the adhesion test.

For durability, as shown by the Steinberg durability test, the tapes treated with Lubricant I of the present invention exhibited the greatest durability at all lubricant levels. This is especially important for magnetic media performance and is therefore highly desirable over prior art lubricants.

Magnetic performance test show that Lubricant I outperformed Lubricant II at the lowest lubricant concentration of 0.55 wt percent for coercivity with magnetic particles of iron metal and barium ferrite; for squareness with barium ferrite and cobalt gamma $Fe_2O_3$; for remanence with cobalt gamma $Fe_2O_3$; and for saturation with iron metal, barium ferrite and cobalt gamma $Fe_2O_3$.

EXAMPLE 5

Dispersions Containing Varying Magnetic Particles To Binder Ratios

Three sets of samples were prepared as in example 4, for each of the magnetic particles (i.e. iron metal, barium ferrite and cobalt gamma $Fe_2O_3$), at magnetic particle to binder ratios of 3:1; 6:1 and 8:1. As in Example 4, samples A-C contained Lubricant II, samples D-F contained Lubricant I and sample G was prepared without lubricant. Sample formulations are set forth in weight (grams) and weight percent. The samples were milled for 4 days, coated onto polyester film and then tested for physical and magnetic properties.

| (Formulations in weight percent) | | | |
|---|---|---|---|
| MAGNETIC PARTICLES:BINDER | 3:1 | 6:1 | 8:1 |
| MAGNETIC PARTICLES | 17.11 | 19.57 | 20.27 |
| SURFACTANT (Re 610) | 0.57 | 0.54 | 0.59 |
| LUBRICANT[a] | 0.57 | 0.54 | 0.59 |
| URETHANE BINDER (Estane) ® | 3.80 | 2.17 | 1.69 |
| VAGH (Vinylchloride/ Vinyl Acetate Copolymer) | 1.09 | 1.09 | 1.84 |
| THF | 76.05 | 76.09 | 76.01 |

[a] Two sets of samples were prepared for each magnetic particles to binder ratio, one set using Lubricant I (cyclophosphazene the present invention) and one set using Lubricant II, (isocetyl stearate).

TABLE A

Physical Test Results

| MAGNETIC PARTICLES:-BINDER RATIO | SLIDING FRICTION | SCRATCH RESISTANCE | ADHESION | STEINBERG 8 min/sec 50 gm. TENSION-TIME TO FAIL IN MIN. |
|---|---|---|---|---|
| IRON METAL | | | | |
| 3:1 Lube II | 0.29 | 500 | PASS | 30 |
| 3:1 Lube I | 0.34 | 450 | PASS | 30 |
| 3:1 None | 0.34 | 500 | FAIL | 30 |
| 6:1 Lube II | 0.34 | 300 | PASS | 10 |
| 6:1 Lube I | 0.36 | 300 | PASS | 19 |
| 6:1 None | 0.36 | 400 | FAIL | 1 |
| 8:1 Lube II | 0.32 | 200 | PASS | 6 |
| 8:1 Lube I | 0.36 | 200 | PASS | 11 |
| 8:1 None | 0.36 | 300 | FAIL | 1 |
| BARIUM FERRITE | | | | |
| 3:1 Lube II | 0.29 | 500 | PASS | 30 |
| 3:1 Lube I | 0.34 | 500 | PASS | 30 |
| 3:1 None | 0.29 | 500 | PASS | 30 |
| 6:1 Lube II | 0.34 | 300 | PASS | 11 |
| 6:1 Lube I | 0.36 | 400 | PASS | 22 |
| 6:1 None | 0.36 | 250 | FAIL | 6 |
| 8:1 Lube II | 0.32 | 200 | FAIL | 10 |
| 8:1 Lube I | 0.36 | 200 | PASS | 14 |
| 8:1 None | 0.34 | 100 | FAIL | 3 |
| COBALT GAMMA $Fe_2O_3$ | | | | |
| 3:1 Lube II | 0.32 | 500 | PASS | 30 |
| 3:1 Lube I | 0.34 | 500 | PASS | 30 |
| 3:1 None | 0.34 | 500 | PASS | 30 |
| 6:1 Lube II | 0.34 | 450 | PASS | 12 |
| 6:1 Lube I | 0.34 | 450 | PASS | 18 |
| 6:1 None | 0.34 | 300 | FAIL | 4 |
| 8:1 Lube II | 0.34 | 250 | FAIL | 6 |
| 8:1 Lube I | 0.36 | 250 | FAIL | 12 |
| 8:1 None | 0.36 | 100 | FAIL | 1 |

TABLE B

MAGNETIC TEST RESULTS

| MAGNETIC PARTICLES:BINDER RATIO | COERCIVITY | SQUARENESS |
|---|---|---|
| IRON METAL | | |
| 3:1 Lube II | 725 | 0.88 |
| 3:1 Lube I | 725 | 0.88 |
| 3:1 None | 730 | 0.81 |
| 6:1 Lube II | 735 | 0.88 |
| 6:1 Lube I | 735 | 0.88 |
| 6:1 None | 740 | 0.82 |
| 8:1 Lube II | 725 | 0.86 |
| 8:1 Lube I | 725 | 0.89 |
| 8:1 None | 730 | 0.80 |
| BARIUM FERRITE | | |
| 3:1 Lube II | 735 | 0.91 |
| 3:1 Lube I | 830 | 0.96 |
| 3:1 None | 780 | 0.85 |
| 6:1 Lube II | 720 | 0.96 |
| 6:1 Lube I | 735 | 0.97 |
| 6:1 None | 735 | 0.81 |
| 8:1 Lube II | 725 | 0.87 |
| 8:1 Lube I | 725 | 0.93 |
| 8:1 None | 725 | 0.80 |
| COBALT GAMMA $Fe_2O_3$ | | |
| 3:1 Lube II | 560 | 0.86 |
| 3:1 Lube I | 565 | 0.85 |
| 3:1 None | 567 | 0.88 |
| 6:1 Lube II | 560 | 0.84 |
| 6:1 Lube I | 570 | 0.85 |
| 6:1 None | 575 | 0.81 |
| 8:1 Lube II | 581 | 0.86 |
| 8:1 Lube I | 585 | 0.85 |
| 8:1 None | 560 | 0.84 |

The test results of Example 5 show generally, for all magnetic particles the lowest friction for the tested magnetic particles-to-binder ratios is obtained with Lubricant II (ICS). Identical results are obtained with cobalt gamma $Fe_2O_3$ at a 6:1 magnetic particles to binder ratio for both Lubricants I and II.

Greatest scratch resistance is shown with for iron metal, with Lubricant II at a magnetic particles-to-binder ratio of 3:1. For ratios of 6:1 and 8:1 scratch resistance was identical for both lubricants. For barium ferrite (at 6:1 ratio) Lubricant I showed best scratch resistance. Identical scratch resistance for Lubricants I and II was obtained for 3:1 and 8:1 ratios. Identical results for cobalt gamma $Fe_2O_3$ were obtained for Lubricants I and II at all ratios. The adhesion results were the same for Lubricants I and II.

Samples containing Lubricant I showed greater durability for all magnetic particles at magnetic particles-to-binder ratios of 6:1 and 8:1. Identical durability results for Lubricants I and II were obtained for 3:1 and 8:1 ratios. For cobalt gamma Fe₂O₃, identical durability results were obtained for Lubricants I and II at all ratios.

Samples containing Lubricant I showed greater durability for all magnetic particles at magnetic particles-to-binder ratios of 6:1 and 8:1. Identical durability for all magnetic particles at magnetic particles-to-binder ratios of 3:1 was shown for Lubricants I and II.

Magnetic performance tests for coercivity produced identical results for iron metal samples with Lubricants I and II. However, Lubricant I produced improved results with all magnetic particles-to-binder ratio samples of barium ferrite and cobalt gamma Fe₂O₃.

Squareness results improved with Lubricant I in iron metal samples at a magnetic particles-to-binder ratio of 8:1; for barium ferrite at all magnetic particles-to-binder ratios; for cobalt gamma Fe₂O₃ at a magnetic particles-to-binder ratio of 6:1. Samples with Lubricant II demonstrated improved squareness only for cobalt gamma Fe₂O₃ at magnetic particles-to-binder ratios of 3:1 and 8:1.

EXAMPLE 6

Dispersions Containing: (1) Lubricant I, (cyclophosphazene lube) (2) Lubricant II (isoceryl stearate) and (3) No Lubricant Dispersions Were prepared at a 4:1 magnetic particles-to-binder ratio as set forth for samples A, D and G discussed above for Example I, using the lubricant level of 3.0 wt percent of magnetic particle lubricant. The samples were milled for 2, 3, and 4 days to evaluate any improvements in milling behavior using the lubricants of the present invention. Formulations are set forth weight percent. Coatings were made after each milling interval and tested as in Examples 4 and 5.

|  | (In Weight Percent) | | |
|---|---|---|---|
|  | PRIOR ART | PRESENT INVENTION | NO LUBRICANT |
| FORMULATIONS | A | D | G |
| MAGNETIC PARTICLES | 18.26 | 18.26 | 18.36 |
| SURFACTANT (Re 610 ®) | 0.55 | 0.55 | 0.55 |
| LUBRICANT I (cyclophosphaze lube) | 0 | 0.55 | 0 |
| URETHANE (Estane ®) | 3.04 | 3.04 | 3.06 |
| VAGH (vinylchloride/ vinyl acetate copolymer) | 1.52 | 1.52 | 1.53 |
| THF | 76.08 | 76.08 | 76.50 |
| LUBRICANT II (isocetyl stearate) | 0.55 | 0 | 0 |

Key A = Lubricant II (isocetyl stearate); D = Lubricant I (cyclophosphazene lube); G = No Lubricant

TABLE A

FOR 2 DAYS MILL TIME
Physical Test Results For Samples After 2 Days Mill Time

| MAGNETIC PARTICLES | SLIDING FRICTION | SCRATCH | ADHESION |
|---|---|---|---|
| IRON METAL | | | |
| A | 0.34 | 300 | PASS |
| D | 0.34 | 200 | PASS |
| G | 0.32 | 200 | FAIL |
| BARIUM FERRITE | | | |
| A | 0.34 | 300 | PASS |
| D | 0.34 | 300 | PASS |
| G | 0.32 | 200 | FAIL |
| COBALT GAMMA Fe₂O₃ | | | |
| A | 0.34 | 300 | PASS |
| D | 0.34 | 300 | PASS |
| G | 0.34 | 200 | FAIL |

TABLE B

FOR 2 DAYS MILL TIME
Magnetic Test Results for Samples After 2 Days Mill Time

|  | COERCIVITY | SQUARENESS |
|---|---|---|
| IRON METAL | | |
| A | 650 | 0.75 |
| D | 660 | 0.72 |
| G | 730 | 0.73 |
| BARIUM FERRITE | | |
| A | 750 | 0.62 |
| D | 690 | 0.57 |
| G | 750 | 0.60 |
| COBALT GAMMA Fe₂O₃ | | |
| A | 575 | 0.62 |
| D | 575 | 0.59 |
| G | 575 | 0.60 |

TABLE A

FOR 3 DAYS MILL TIME
Physical Test Results For Samples After 3 Days Mill Time

| MAGNETIC PARTICLES | SLIDING FRICTION | SCRATCH | ADHESION |
|---|---|---|---|
| IRON METAL | | | |
| A | 0.32 | 350 | PASS |
| D | 0.32 | 250 | PASS |
| G | 0.32 | 200 | PASS |
| BARIUM FERRITE | | | |
| A | 0.34 | 450 | PASS |
| D | 0.34 | 450 | PASS |
| G | 0.32 | 300 | PASS |
| COBALT GAMMA | | | |

TABLE A-continued

FOR 3 DAYS MILL TIME
Physical Test Results For Samples After 3 Days Mill Time

| MAGNETIC PARTICLES | SLIDING FRICTION | SCRATCH | ADHESION |
|---|---|---|---|
| $Fe_2O_3$ | | | |
| A | 0.34 | 500 | PASS |
| D | 0.34 | 500 | PASS |
| G | 0.34 | 450 | PASS |

TABLE B

FOR 3 DAYS MILL TIME
Magnetic Test Results for Samples After 3 Days Mill Time

| | COERCIVITY | SQUARENESS |
|---|---|---|
| IRON METAL | | |
| A | 700 | 0.77 |
| D | 720 | 0.73 |
| G | 750 | 0.74 |
| BARIUM FERRITE | | |
| A | 775 | 0.85 |
| D | 690 | 0.89 |
| G | 750 | 0.74 |
| COBALT GAMMA $Fe_2O_3$ | | |
| A | 600 | 0.81 |
| D | 575 | 0.86 |
| G | 625 | 0.80 |

TABLE A

FOR 4 DAYS MILL TIME
Physical Test Results For Samples After 4 Days Mill Time

| MAGNETIC PARTICLES | SLIDING FRICTION | SCRATCH | ADHESION |
|---|---|---|---|
| IRON METAL | | | |
| A | 0.29 | 500 | PASS |
| D | 0.29 | 500 | PASS |
| G | 0.34 | 500 | PASS |
| BARIUM FERRITE | | | |
| A | 0.32 | 500 | PASS |
| D | 0.32 | 500 | PASS |
| G | 0.34 | 500 | PASS |
| COBALT GAMMA $Fe_2O_3$ | | | |
| A | 0.32 | 500 | PASS |
| D | 0.32 | 500 | PASS |
| G | 0.34 | 500 | PASS |

TABLE B

FOR 4 DAYS MILL TIME
Magnetic Test Results for Samples After 4 Days Mill Time

| | COERCIVITY | SQUARENESS |
|---|---|---|
| IRON METAL | | |
| A | 740 | 0.79 |
| D | 750 | 0.74 |
| G | 760 | 0.75 |
| BARIUM FERRITE | | |
| A | 800 | 0.90 |
| D | 690 | 0.98 |
| G | 800 | 0.87 |
| COBALT GAMMA $Fe_2O_3$ | | |
| A | 625 | 0.91 |
| D | 600 | 0.91 |
| G | 625 | 0.89 | physical test results after 2 and 3 days showed improved scratch resistance for Lubricant II with iron metal. Both lubricants performed equally well for scratch resistance in the barium ferrite and cobalt gamma $Fe_2O_3$ magnetic particles at 2 and 3 days, and for all magnetic particles after 4 days.

Magnetic test results for Lubricant I showed improved coercivity for iron metal at 2, 3, and 4 days and improved squareness for barium ferrite after 3 and 4 days.

EXAMPLE 7

Evaluation of Our Lubricant As A Surface Coating

Magnetic recording media rigid disks prepared as Sample G in Examples 4, 5, and 6 using no lubricant were submerged in a 5% lubricant solution and then spun. Separate samples were prepared with Lubricant I of the present invention and with Krytox 143AD, a hexafluoropropylene epoxide polymer, and tested.

TEST RESULTS

| MAGNETIC PARTICLES | SURFACE COATING | FRICTION | SCRATCH | STEINBERG 8 min/sec 50 gm. TENSION-TIME TO FAIL IN MIN. |
|---|---|---|---|---|
| IRON METAL | LUBE I | 0.24 | 200 | 30 MIN |
| | KRYTOX[a] | 0.31 | 100 | 16 MIN |
| | NO LUBE | 0.34 | 100 | 4 MIN |
| BARIUM FERRITE | LUBE I | 0.24 | 400 | 30 MIN |
| | KRYTOX[a] | 0.31 | 300 | 16 MIN |
| | NO LUBE | 0.34 | 300 | 4 MIN |
| COBALT GAMMA $Fe_2O_3$ | LUBE I | 0.19 | 250 | 28 MIN |
| | KRYTOX[a] | 0.26 | 100 | 19 MIN |
| | NO LUBE | 0.34 | 100 gm | 6 MIN |

[a]Krytox is a hexafluoropropylene epoxide polymer. Krytox is a registered trademark of the DuPont DeNemours, E. I. and Co., Wilmington, De.

Test results show that Lubricant I of the present invention provides improved physical performance over the Krytox lubricant as a surface coating for magnetic media. Lubricant I is superior to Krytox in physical performance as it reduces friction, increases scratch resistance and increases durability.

As shown in Example 4, Table A, samples containing Lubricant I as a boundary lubricant exhibits superior physical durability in comparison to those samples with Lubricant II. Further, as shown in Table B, Lubricant I containing samples exhibited superior magnetic performance at the lowest levels, showing the best values for: coercivity with iron metal and barium ferrite; squareness with barium ferrite and cobalt gamma $Fe_2O_3$;

remanance with cobalt gamma Fe2O3; and saturation for all three types of magnetic particles. As an overcoat lubricant, Lubricant I of the present invention is clearly superior to Krytox. As shown in Example 7, Lubricant I shows reduced friction and improved scratch resistance and durability.

Thus, there is provided in accordance with the present invention, an advanced form of recording media and lubricant for the media, which provide more efficient internal and boundary lubricant systems to improve performance and reduce wear.

While our invention has been described in terms of a specific embodiment, it will be appreciated that other embodiments could be readily adapted by one skilled in the art. Accordingly, the scope of our invention is to be limited only by the following claims.

We claim:

1. A magnetic recording media, comprising:
   a substrate; and
   a magnetic recording lamina thereon, said lamina including
   (a) magnetic particles for recording information,
   (b) a binder for dispersing the magnetic particles, and
   (c) a lubricating amount of a cyclic phosphazene compound, said cyclic phosphazene compound being completely substituted with
      (1) fluorinated phenoxy substituents selected from the group consisting of monofluorinated phenoxy, difluorinated phenoxy, triflourinated phenoxy, tetraflourinated phenoxy and pentafluorinated phenoxy, and
      (2) m-perfluoroalkylphenoxy substituents, said substituents being present in a ratio of fluorinated phenoxy to m-perfluoroalkyl phenoxy ranging from about 1:1 to about 1:5.

2. The magnetic recording media of claim 1, wherein the cyclic phosphazene compound corresponds to the following formula:

wherein n is 3 through 7, and R is individually selected in each occurrence from the group consisting of fluorinated phenoxy and m-perfluoroalkyl-phenoxy, such that the ratio of the fluorinated phenoxy to m-perfluoroalkylphenoxy substituents ranges from about 1:1 to about 1:5.

3. The magnetic recording media of claim 1, wherein the ratio of fluorinated phenoxy to m-perfluoroalkylphenoxy is about 1:2.

4. The magnetic recording media of claim 1 wherein the fluorinated phenoxy substituent is monofluorinated phenoxy.

5. The magnetic recording media of claim 4, wherein the fluorinated phenoxy substituent is a monofluorinated phenoxy including m-fluorophenoxy.

6. The magnetic recording media of claim 4, wherein the fluorinated phenoxy substituent is a monofluorinated phenoxy including o-fluorophenoxy.

7. The magnetic recording media of claim 4, wherein the fluorinated phenoxy substituent is a monofluorinated phenoxy including p-fluorophenoxy.

8. The magnetic recording media of claim 1, wherein the m-perfluoroalkylphenoxy substituents are trifluoromethylphenoxy substituents.

9. The magnetic recording media of claim 2, wherein n is 3.

10. The magnetic recording media of claim 2, wherein n is 4.

11. The magnetic recording media of claim 1, wherein the cyclic phosphazene includes 2,2,4,4,6,6-di(4-fluorophenoxy)tetra(3-trifluoromethylphenoxy)-1,3,5-triaza-2,4,6-triphosphorine.

12. The magnetic recording media of claim 1, wherein the cyclic phosphazene includes 2,2,4,4,6,6-di(3-fluorophenoxy)tetra(3-trifluoromethylphenoxy)-1,3,5-triaza-2,4,6-triphosphorine.

13. The magnetic recording media of claim 1, wherein the cyclic phosphazene includes 2,2,4,4,6,6-(3-fluorophenoxy) (4-fluorophenoxy) tetra(3-trifluoromethylphenoxy)-1,3,5-triaza-2,4,6-triphosphorine.

14. The magnetic recording media of claim 4, wherein the cyclic phosphazene includes 2,2,4,4,6,6-tri(3-fluorophenoxy)tri(3-trifluoromethyl-phenoxy)-1,3,5-triaza-2,4,6-triphosphorine.

15. The magnetic recording media of claim 4, wherein the cyclic phosphazene includes 2,2,4,4,6,6-mono(fluorophenoxy)penta(3-trifluoromethyl-phenoxy)-1,3,5-triaza-2,4,6-triphosphorine.

16. The magnetic recording media of claim 1, wherein the magnetic particle to binder ratio is between about 3:1 and 8:1.

17. The magnetic recording media of claim 1, wherein the magnetic particle to binder ratio is between about 3:1 and about 5:1.

18. The magnetic recording media of claim 1, wherein the magnetic particles are present in an amount ranging from about 17.0 to 21.0 weight percent based on total composition weight including solvent.

19. The magnetic recording media of claim 1, wherein the fluorophenoxy substituted cyclophosphazene lubricant is present in an amount between about 0.50 and about 1.0 weight percent based on total composition weight.

* * * * *